US006051676A

United States Patent [19]

Sirianni

[11] Patent Number: 6,051,676
[45] Date of Patent: Apr. 18, 2000

[54] METHOD FOR REDUCING BLEACH MALODOR ON SKIN

[75] Inventor: Giuseppe Sirianni, Gimigliano, Italy

[73] Assignee: The Procter & Gamble Company, Cincinnati, Ohio

[21] Appl. No.: 09/202,020

[22] PCT Filed: Jun. 6, 1997

[86] PCT No.: PCT/US97/09870

§ 371 Date: Mar. 2, 1999

§ 102(e) Date: Mar. 2, 1999

[87] PCT Pub. No.: WO97/47685

PCT Pub. Date: Dec. 18, 1997

[30] Foreign Application Priority Data

Jun. 10, 1996 [EP] European Pat. Off. ............. 96870072

[51] Int. Cl.[7] ..................................... C08G 64/00

[52] U.S. Cl. .......................... 528/196; 528/198; 525/439; 525/461

[58] Field of Search ................................... 528/196, 198; 525/439, 461

[56] References Cited

U.S. PATENT DOCUMENTS 5,348,682   9/1994   Finley et al. ....................... 252/186.36

*Primary Examiner*—Terressa M. Boykin
*Attorney, Agent, or Firm*—Richard S. Echler, Sr.; Kim William Zerby; Jacobus C. Rasser

[57] ABSTRACT

The present invention relates to the use of a polycarboxylate polymer in a hypochlorite bleach containing composition to reduce bleach malodour from the contacting of said composition with skin surfaces.

7 Claims, No Drawings

METHOD FOR REDUCING BLEACH MALODOR ON SKIN

FIELD OF THE INVENTION

The present invention relates to the use of polycarboxylate polymers in hypochlorite bleach containing-compositions to reduce malodour arising from the contacting of said bleach composition with skin.

BACKGROUND OF THE INVENTION

Efficient cleaning is one of the requirement which drives consumer acceptance of cleaning products. Such a requirement is necessary to provide compositions with a broad spectrum of soil removal such as greasy and oily soils respectively present on the kitchen and bathroom surfaces. To fulfill such cleaning requirement, products containing hypochlorite bleach have been formulated, wherein such hypochlorite component serves as a strong oxidiser to assist in the chemical degradation, break-up and removal of stains and soils. A further advantage to the use of said hypochlorite component in cleaning products is that it also serves as an effective disinfectant. However, a problem encountered with the use of such bleach-containing composition is that of the resulting bleach malodour on the hands produced by contacting the liquid composition with the hands, even after several rinses. Numerous solutions have been proposed in the art to solve the problem of bleach malodour.

One solution has been proposed with the use of a volatile perfume composition in hypochlorite bleach containing composition as described in EP 439 878.

Another solution has been described in EP 606 707 which provides a composition, comprising a polymeric component together with a hypochlorite compound, exhibiting reduced in-product bleach malodour as well as reduced bleach malodour on the cleaned surface. Such benefit is believed to be due to the high yield viscosity of the composition which trap the bleach molecules responsible of bleach malodour within vesicles.

The overall emphasis in the above prior art has thus been on the reduction of the bleach malodour within the product composition or on the hard surface to be cleaned and relatively little attention has been paid to the reduction of bleach malodour arising from the contacting of said composition with skin surfaces, such as hands.

It is therefore an object of the invention to reduce the bleach malodour on skin surfaces arising from the contacting of a hypochlorite containing-cleaning composition with said surfaces.

JP 63108099 describes the use of sulfamic acid or its salt for reducing the chlorine odour emitted from hypochlorite containing-solutions or when said hypochlorite containing-solutions are in contact with the skin.

The Applicant has now found that the use of a polycarboxylate polymer in a hypochlorite bleach containing-cleaning composition fulfills such a need.

SUMMARY OF THE INVENTION

The present invention relates to the use of a polycarboxylate polymer in a hypochlorite bleach containing composition to reduce bleach malodour arising from the contacting of said composition with skin surfaces.

DETAILED DESCRIPTION OF THE INVENTION

Polycarboxylate Polymer

The essential component for use herein is a polycarboxylate polymer. The polymers preferably have a molecular weight of from 500.000 to 4.500.000, preferably from 1.000.000 to 4.000.000. Most preferred polymers for use herein contain from 0.5% to 4% by weight of a cross-linking agent, wherein the cross-linking agent tends to interconnect linear strands of the polymers to form the resulting cross-linked products. Suitable cross-linking agents include the polyalkenyl polyethers. Polycarboxylate polymers include the polyacrylate polymers. Others monomers besides acrylic acid can be used to form these polymers including such monomers as maleic anhydride which acts as a source of additional carboxylic groups. The molecular weight per carboxylate group of monomers containing a carboxylate group typically varies from 25 to 200, preferably from 50 to 150, more preferably from 75 to 125. Further other monomers may be present in the monomeric mixture, if desired, such as ethylene and propylene which act as diluents.

Preferred polycarboxylate polymers for use herein are the polyacrylate polymers. Commercially available polymers of the polyacrylate type include those sold under the trade names Carbopol®, Acrysol® ICS-1, Polygel®, and Sokalan®. Most preferred polyacrylate polymers are the copolymer of acrylic acid and alkyl ($C_5$–$C_{10}$) acrylate, commercially available under the tradename Carbopol® 1623, Carbopol® 695 from BF Goodrich, and Polygel ® DB available from 3V Chemical company.

Mixtures of any of the polycarboxylate polymers, herein before described, may also be used.

The polycarboxylate polymeric components have surprisingly been found effective in reducing the bleach malodour on skin surfaces resulting from the contacting of the skin with hypochlorite containing-composition upon a cleaning process. Accordingly, the polycarboxylate is incorporated in a hypochlorite containing-composition. The polymer is present in an amount of from 0.1% to 4% by weight, preferably 0.4% to 1.5% by weight of the composition.

Hypochlorite

The hypochlorite bleaching agent is an alkali metal hypochlorite. Although alkali metal hypochlorites are preferred, other hypochlorite compounds may also be used herein and can be selected from calcium and magnesium hypochlorite. A preferred alkali metal hypochlorite for use herein is sodium hypochlorite. The compositions to be used herein will comprise said hypochlorite bleaching agent in a sufficient amount such that the content of active chlorine in the compositions is from 0.1% to 10%, preferably 0.1% to 5%, more preferably from 1% to 2% by weight.

Optionals

The compositions may also comprise a number of optional ingredients conventional to the cleaning compositions such as surface-active agents, organic acids, fatty acids, radical scavengers, antimicrobial compounds, builders, chelants, buffers, bactericides, solvents, enzymes, hydrotropes, colorants, bleach activators, soil suspenders, dye transfer agents, brighteners, anti dusting agents, dispersants, dye transfer inhibitors, pigments, perfumes and dyes.

Surface active agents are useful as cleaning components. Preferred surface active agents are the surfactants having hypochlorite stability, e.g surfactants which contain no functionalities (such as ether linkages, unsaturation, some aromatic structures or hydroxyl groups) which are susceptible of oxidation by the hypochlorite bleach. Typical hypochlorite compatible surfactants include the alkyl sulphates, amine oxides and mixtures thereof. Typical level of surfactants within the composition is from 0.1% to 10% by weight.

The composition may also optionally comprises organic acids. Such components will provide a further reduction of the bleach malodour. When used, said components will be present in an amount of from 0.1% to 10% by weight. Typical organic acids include hydrochloric acid, citric acid, phosphoric acid, the maleic derivatives such as maleic acid, maleic anhydride, the sulfonic acids derivatives such as sulfamic acid, methanesulfonic acid and mixtures thereof.

An optional requirement of the compositions to be used herein is that the pH is greater than 10, preferably greater than 11, more preferably greater than 12. This is achieved by the addition of from 0.4% to 2% of a caustic alkali. Suitable caustic alkalis for use herein include sodium and potassium hydroxide. Compositions for the purpose of the present invention preferably have a pH greater than 12 for hypochlorite stability.

Packaging form of the Compositions

The compositions herein may be packaged in a variety of suitable detergent packaging known to those skilled in the art. When present in liquid form, the compositions herein may desirably be packaged in manually operated spray dispensing containers, which are usually made of synthetic organic polymeric plastic materials. Typical types of dispensers are disclosed, for instance, in U.S. Pat. No. 4,701,311 to Dunnining et al. and U.S. Pat. No. 4,646,973 and U.S. Pat. No. 4,538,745 both to Focarracci.

Reduction of the Bleach Malodour on Skin Surface

The benefit provided by the use of the present invention is that the residual bleach malodour which arises on skin surfaces such as hands is reduced, i.e. the skin which is in contact with a composition containing a hypochlorite bleaching component and a polycarboxylate polymer exhibits a reduced residual bleach malodour versus the skin which is in contact with the same composition without polycarboxylate polymer.

Not to be bound by theory, it is believed that the mechanism for producing the benefits of the invention is different to that of the mechanism for producing reduced bleach malodour within the product and on the cleaned hard surfaces. Hence, whilst the reduction of hypochlorite bleach malodour within the product or on the cleaned surface is due, as specified in EP 606 707, to the high yield value which trapped the malodorous hypochlorite bleach molecules within its vesicles; the reduction of hypochlorite bleach malodour on the skin surfaces is believed to follow a different mechanism.

The mechanism for producing the benefit of the invention is believed to be as follows: upon use of the composition containing a hypochlorite bleach and a polycarboxylate polymer, the polycarboxylate polymer forms a hydrophobic film on the hands surface. As a result, the contact with the water phase containing the hypochlorite is reduced; which thus, slows the kinetics of reaction between the hypochlorite and the skin amino acid; the volatile product reaction of said hypochlorite and the skin amino acid being the cause of the residual bleach malodour on hands.

The bleach malodour reduction benefit can be assessed using the following method:

Bleach malodour reduction test method:

The method is comparative and thus only one composition's odour respective to another may be tested at any one time. The odour is evaluated using the following scale:

0 No bleach odour
1 Very weak bleach odour
2 Weak bleach odour
3 Moderate bleach odour
4 Strong bleach odour
5 Very strong bleach odour Residual odour on hands evaluation:

The hypochlorite comprising composition is diluted, 1 part to 25 parts water. Sufficient solution is made to fill a container to a level to submerge the hands and wrists of the tester. The tester places one hand into each of the solutions to be tested for 30 seconds. The hands are then removed from the solution and placed under cold running water for 5 seconds. Each hand is patted dry with paper towels. The hands are then smelt by a grading panel of 6 persons at time intervals of 0, 15, 30, 45, 60, 90 and 120 minutes. A rating for odour is then given using the above scale. After 3 hours the hands are rewetted and smelt. The test is then repeated.

In the detergent compositions of the invention, the abbreviated component identifications have the following meanings:

C8 AS: Octyl sulphate, available from Albright and Wilson, under the tradename Empimin® LV33

24 AS: Sodium $C_{12}$–$C_{14}$ alkyl sulphate, available from Albright and Wilson, under the tradename Empicol® 0298/F 24E3S: $C_{12}$–$C_{14}$ sodium alkyl sulphate condensed with an average of 3 moles of ethylene oxide per mole Amine oxide: $C_{12}$–$C_{14}$ amine oxide, commercially available under the tradename Genaminox® LA from Hoechst Polymer: Copolymer of acrylic acid and alkyl ($C_5$–$C_{10}$) acrylate, commercially available under the tradename Carbopol® 1623 from BF Goodrich Fatty acid: $C_8$–$C_{18}$ fatty acid nonionic: Capped ethoxylated carboxylate of formula $C_{12}$–$C_{14}(OCH_2CH_2)_xCH_2COOR$, wherein x is an integer ranging from 2 to 4

The invention is illustrated in the following non limiting examples, in which all percentages are on a weight basis unless otherwise stated.

EXAMPLE 1

Using the test method defined above, hands were contacted with a cleaning composition and thereafter evaluated for their bleach malodour reduction.

The compositions had the following formulation:

| Components | A | B | C | D | E | F |
| --- | --- | --- | --- | --- | --- | --- |
| 24 AS | — | 1.0 | 2.0 | 2.0 | 1.0 | 1.0 |
| C8 AS | 2.0 | 1.0 | 1.0 | 2.0 | 2.0 | 2.0 |
| Polymer | 0.8 | 0.8 | 1.2 | 1.0 | 1.0 | 1.0 |
| Caustic | — | 1.4 | 1.4 | 1.5 | 1.4 | — |
| Sodium hypochlorite | 1.0 | 1.4 | 1.0 | 1.0 | 1.4 | 1.4 |
| Fatty acid | — | 0.2 | 0.3 | 0.3 | 0.2 | — |
| Water and minors up to 100 | | | | | | |

It was observed that hands contacted with hypochlorite compositions containing a polycarboxylate polymer exhibited a reduced hypochlorite bleach malodour versus hypochlorite compositions which did not contain a polycarboxylate polymer. Such a benefit was observed on rinsed hands as well as non rinsed hands.

EXAMPLE 2

Similar results were observed where the following compositions were used.

|  | G | H | I | J | K | L | M | N | O |
|---|---|---|---|---|---|---|---|---|---|
| Amine oxide | — | — | — | — | 0.4 | 0.4 | 0.8 | 0.8 | 0.8 |
| C8 AS | — | 1.0 | 2.0 | 2.0 | — | 2.0 | 2.0 | 2.0 | 2.0 |
| 24AE3S | 2.0 | 2.0 | 1.0 | 1.0 | — | — | — | 2.0 | — |
| 24AS | — | — | — | — | — | — | 2.0 | — | — |
| Polymer | 0.8 | 1.0 | 1.2 | 1.0 | 0.8 | 0.8 | 0.8 | 0.8 | 0.8 |
| nonionic | 0.5 | 0.5 | 1.0 | 1.0 | — | — | — | — | 2.0 |
| fatty acid | 0.3 | 0.3 | 0.3 | 0.3 | — | — | — | — | — |
| Caustic | 1.4 | 1.4 | 1.4 | 1.4 | 1.4 | 1.4 | 1.4 | 1.4 | 1.4 |
| sodium hypochlorite | 1.4 | 1.6 | 1.6 | 1.4 | 1.4 | 1.4 | 1.4 | 1.4 | 1.4 |

Water and minors up to 100

What is claimed is:

1. A method for reducing malodor formation on skin comprising the step of cleaning a surface with a composition which does not form malodor when in contact with skin, said composition comprising:
   a) from 0.1% to 4% by weight, of a polycarboxylate polymer, said polycarboxylate polymer is a polyacrylate polymer having a molecular weight of from 200,000 daltons to 5,000,000 daltons;
   c) a hypochlorite bleaching agent in an amount sufficient to provide from 0.1% to 10% by weight, of said cleaning composition, active chlorine, and
   d) the balance carriers and other adjunct ingredients.

2. A method according to claim 1 wherein said polycarboxylate polymer is a polyacrylate polymer.

3. A method according to claim 1 comprising from 0.4% to 1.5% by weight, of said polycarboxylate polymer.

4. A method according to claim 1 further comprising a hypochlorite bleaching agent in an amount sufficient to provide from 0.1% to 5% by weight, of said cleaning composition, active chlorine.

5. A method according to claim 1 wherein said composition has a pH of greater than 10.

6. A method according to claim 1 wherein said adjunct ingredients are selected from the group consisting of surface-active agents, organic acids, fatty acids, radical scavengers, antimicrobial compounds, builders, chelants, buffers, bactericides, solvents, enzymes, hydrotropes, colorants, bleach activators, soil suspenders, dye transfer agents, brighteners, anti dusting agents, dispersants, dye transfer inhibitors, pigments, perfumes, dyes, and mixtures thereof.

7. A method for reducing malodor formation on skin comprising the step of cleaning a surface with a composition which does not form malodor when in contact with skin, said composition comprising:
   a) from 0.1% to 4% by weight, of a polycarboxylate polymer, said polycarboxylate polymer is a polyacrylate polymer having a molecular weight of from 200,000 daltons to 5,000,000 daltons;
   c) a hypochlorite bleaching agent in an amount sufficient to provide from 0.1% to 10% by weight, of said cleaning composition, active chlorine, and
   d) the balance carriers and other adjunct ingredients, said adjunct ingredients selected from the group consisting of surface-active agents, organic acids, fatty acids, radical scavengers, antimicrobial compounds, builders, chelants, buffers, bactericides, solvents, enzymes, hydrotropes, colorants, bleach activators, soil suspenders, dye transfer agents, brighteners, anti dusting agents, dispersants, dye transfer inhibitors, pigments, perfumes, dyes, and mixtures thereof, provided said composition has a pH of greater than 10.

* * * * *